United States Patent
Kamada et al.

(10) Patent No.: US 9,773,710 B2
(45) Date of Patent: Sep. 26, 2017

(54) METHOD FOR EVALUATING CONCENTRATION OF DEFECT IN SILICON SINGLE CRYSTAL SUBSTRATE

(71) Applicant: SHIN-ETSU HANDOTAI CO., LTD., Tokyo (JP)

(72) Inventors: Hiroyuki Kamada, Nishigo-mura (JP); Ryoji Hoshi, Nishigo-mura (JP)

(73) Assignee: SHIN-ETSU HANDOTAI CO., LTD., Tokyo (JP)

( * ) Notice: Subject to any disclaimer, the term of this patent is extended or adjusted under 35 U.S.C. 154(b) by 0 days.

(21) Appl. No.: 15/036,915

(22) PCT Filed: Nov. 12, 2014

(86) PCT No.: PCT/JP2014/005680
§ 371 (c)(1),
(2) Date: May 16, 2016

(87) PCT Pub. No.: WO2015/087485
PCT Pub. Date: Jun. 18, 2015

(65) Prior Publication Data
US 2016/0300768 A1 Oct. 13, 2016

(30) Foreign Application Priority Data
Dec. 10, 2013 (JP) .................. 2013-255250

(51) Int. Cl.
*G01N 27/04* (2006.01)
*G01N 15/06* (2006.01)
(Continued)

(52) U.S. Cl.
CPC ............. *H01L 22/12* (2013.01); *G01N 15/06* (2013.01); *G01N 27/00* (2013.01); *G01N 27/04* (2013.01);
(Continued)

(58) Field of Classification Search
CPC ........ G01N 27/00; G01N 27/02; G01N 27/04; G01N 27/041; G01N 15/06; G01N 17/00;
(Continued)

(56) References Cited

U.S. PATENT DOCUMENTS 7,244,306 B2 * 7/2007 Kurita ................... C04B 24/003
117/13
8,771,415 B2 * 7/2014 Umeno ................... C30B 15/00
117/13
(Continued)

FOREIGN PATENT DOCUMENTS

JP H08-102545 A 4/1996
JP H09-55415 A 2/1997
(Continued)

OTHER PUBLICATIONS

Feb. 10, 2015 Search Report issued in International Patent Application No. PCT/JP2014/005680.
(Continued)

*Primary Examiner* — Hoai-An D Nguyen
(74) *Attorney, Agent, or Firm* — Oliff PLC (57) ABSTRACT

A method for evaluating concentration of defect in silicon single crystal substrate, defect being formed by particle beam irradiation in silicon single crystal substrate, including the steps of: measuring a resistivity of silicon single crystal substrate, followed by irradiating silicon single crystal substrate with particle beam, re-measuring resistivity of silicon single crystal substrate after irradiation; determining each carrier concentration in silicon single crystal substrate before and after irradiation on basis of measured results of resistivity before and after particle beam irradiation to calculate rate of change of carrier concentration; and evaluating concentration of VV defect on basis of rate of change of carrier concentration, VV defect being made of a silicon atom vacancy and being formed by particle beam irradiation
(Continued)

in silicon single crystal substrate. The method can simply evaluate concentration of VV defect formed in silicon single crystal substrate by particle beam irradiation.

8 Claims, 3 Drawing Sheets

(51) Int. Cl.
  *H01L 21/66* (2006.01)
  *G01N 27/00* (2006.01)
  *H01L 33/02* (2010.01)
(52) U.S. Cl.
  CPC ........... *G01N 27/041* (2013.01); *H01L 22/14* (2013.01); *H01L 33/025* (2013.01)
(58) Field of Classification Search
  CPC .. G01N 17/004; G01N 17/006; G01N 17/008; G01N 33/48735; H01L 22/00; H01L 22/10; H01L 22/12; H01L 22/14; H01L 29/00; H01L 29/02; H01L 29/06; H01L 29/0603; H01L 29/086; H01L 29/0878; H01L 29/36; H01L 33/00; H01L 33/02; H01L 33/025
  USPC .... 324/600, 649, 691, 693, 71.1, 71.3, 71.4, 324/71.5; 117/11, 13, 14, 54, 74; 702/1, 702/22, 23
  See application file for complete search history.

(56) References Cited

U.S. PATENT DOCUMENTS

| | | | |
|---|---|---|---|
| 9,111,883 B2* | 8/2015 | Hoshi | ................. C30B 29/06 |
| 2009/0064786 A1* | 3/2009 | Goto | ................. G01N 29/041 73/597 |
| 2012/0112135 A1* | 5/2012 | Sakurada | ................. C30B 11/06 252/512 |
| 2014/0379276 A1* | 12/2014 | Hoshi | ................. H01L 22/14 702/23 |
| 2015/0316511 A1* | 11/2015 | Guo | ................. H04B 10/27 398/140 |

FOREIGN PATENT DOCUMENTS

| | | |
|---|---|---|
| JP | 2008-177296 A | 7/2008 |
| JP | 2012-199299 A | 10/2012 |

OTHER PUBLICATIONS

Nakamura, M. et al., "Photoluminescence Measurement of Carbon in Silicon Crystals Irradiated with High Energy Electrons", J. Electrochem. Soc., 1994, vol. 141, No. 12, pp. 3576-3580.
Ishino, S., "shousha sonshou", University of Tokyo Press, 1979, pp. 178-183.

* cited by examiner

METHOD FOR EVALUATING CONCENTRATION OF DEFECT IN SILICON SINGLE CRYSTAL SUBSTRATE

TECHNICAL FIELD

The present invention relates to a method for evaluating a concentration of a crystal defect introduced into a silicon single crystal substrate by irradiation of a particle beam comprised of an electron, an ion, etc.

BACKGROUND ART

In manufacturing process of semiconductor devices such as PN diodes or IGBTs, irradiation with an electron beam or various particle beams such as a proton beam and a helium ion beam can be performed in order to control their carrier lifetime. For example, Patent Document 1 discloses a PN diode in which crystal defects are formed near the interface of the PN junction by implanting protons. Irradiation to silicon crystals with a particle beam introduces crystal defects, and decreases the carrier lifetime accordingly. A desirable lifetime can be obtained by controlling the irradiation quantity.

The following is a process to form a defect in a silicon single crystal with particle beam irradiation. First, when particle beams are implanted, silicon atoms composing a crystal is sprung out from the lattice position to form interstitial silicons (I) and monovacancies (V). This pair of the interstitial silicon and the monovacancy is referred to as a Frenkel pair.

A part of the interstitial silicons is replaced to a carbon atom Cs existing at the lattice position to form an interstitial carbon Ci. This interstitial carbon is unstable, and accordingly bonds to an interstitial oxygen or other substitutional carbon to form a composite defect such as CiOi or CiCs respectively. It is considered that the rest of the interstitial silicons will form clusters by agglomerating with other interstitial silicons, remain intact in the crystals, or bond with monovacancies again to disappear.

It is known that the defects due to interstitial carbons such as CiOi and CiCs can be detected by photoluminescence (PL) or cathode luminescence (CL) and are influenced by oxygen concentration or carbon concentration in the crystal (Non-Patent Document 1).

On the other hand, it is considered that the monovacancy in the Frenkel pair comes to be stable state when the monovacancy locates in a particular position with another monovacancy, and many of them form VV defects composed of two silicon atom vacancies. There is an example to evaluate this defect by electron spin resonance (ESR) analysis (Non-Patent Document 2).

CITATION LIST

Patent Literature

Patent Document 1: Japanese Unexamined Patent Publication (Kokai) No. H08-102545
Non-Patent Document 1: M. Nakamura et al., J. Electrochem. Soc., Vol. 141, No. 12, 3576 (1994)
Non-Patent Document 2: S. Ishino, "shousha sonshou", University of Tokyo Press (1979), p 178-183

SUMMARY OF INVENTION

Technical Problem

As described above, the crystal defect due to irradiation comes to be a carrier trap and plays a role to decrease the lifetime. Although these amounts have to be controlled in power devices, etc. in order to set the lifetime to an appropriate value, there has been a problem that the formed amount of VV defects is difficult to be evaluated quantitatively compared to that of the defects related to carbon which can be quantified to a certain degree by evaluation methods such as CL.

The present invention was accomplished in view of the above-described problems. It is an object of the present invention to provide a method which can simply evaluate a concentration of a VV defect formed by particle beam irradiation in the silicon single crystal substrate.

Solution to Problem

To solve the problems, the present invention provides a method for evaluating a concentration of a defect in a silicon single crystal substrate, the defect being formed by particle beam irradiation in the silicon single crystal substrate, comprising the steps of: measuring a resistivity of the silicon single crystal substrate, followed by irradiating the silicon single crystal substrate with the particle beam, re-measuring resistivity of the silicon single crystal substrate after the irradiation; determining each carrier concentration in the silicon single crystal substrate before and after the irradiation on the basis of the measured results of resistivity before and after the particle beam irradiation to calculate a rate of change of the carrier concentration; and evaluating a concentration of a VV defect on the basis of the rate of the change of the carrier concentration, the VV defect being comprised of a silicon atom vacancy and being formed by the particle beam irradiation in the silicon single crystal substrate.

As described above, the present invention can evaluate the VV defect concentration on the basis of measurement of the resistivities before and after the particle beam irradiation and the rate of the change of the carrier concentration obtained by the measured resistivities, and is a very simple evaluation method accordingly. Furthermore, it is possible to obtain the relation of the VV defect concentration with an irradiation quantity of a particle beam or a crystal quality (such as an oxygen concentration) from the evaluation result.

The particle beam to irradiate the silicon single crystal substrate can be composed of an electron or an ion.

Such particle beam irradiation enables to form a Frenkel pair and a VV defect due to a monovacancy V of the Frenkel pair in a silicon single crystal substrate.

A dopant impurity contained in the silicon single crystal substrate can be any of phosphorous, arsenic, and antimony.

Using such dopant impurities, each of which has the same or larger atomic radius compared to silicon and can form a complex with a monovacancy to be stabilized, the evaluation of the VV defect concentration using the rate of the change of the carrier concentration can be performed more securely.

It is also possible for the inventive method to further comprise the steps of: preparing a silicon single crystal substrate for pre-examination with a pre-evaluated concentration of the VV defect separately from the silicon single crystal substrate to be evaluated; determining a correlation on the basis of the pre-evaluated concentration of the VV defect and a rate of change of a carrier concentration before and after the particle beam irradiation with respect to the silicon single crystal substrate for pre-examination; and irradiating the silicon single crystal substrate to be evaluated with the particle beam to evaluate the concentration of the VV defect by using the correlation.

Using a result of such pre-examination, the relative evaluation of the VV defect concentration in the silicon single crystal substrate to be evaluated can be performed more simply.

Advantageous Effects of Invention

As described above, by the present invention, it is possible to evaluate a concentration of VV defects due to particle beam irradiation in a simple way, and to obtain the relation of the VV defect concentration with an irradiation quantity of the particle beam or a crystal quality. This enables to more simply grasp a required irradiation quantity or a crystal quality so as to control the lifetime of a silicon single crystal substrate to a desired value.

DESCRIPTION OF EMBODIMENTS

The embodiment of the present invention will be explained in the following, but the present invention is not limited thereto.

First, it will be described how the inventors have accomplished the present invention.

As described above, it has been considered previously that many of Vs (monovacancies) of the Frenkel pairs formed by particle beam irradiation form VV defects. However, the present inventors have diligently investigated and found that the Vs mainly bring three reactions of (1) V+O→VO, (2) V+X→VX, and (3) V+V→VV. In these formulae, O represents an oxygen atom, X represents a dopant atom.

Herein, the amount of each impurity element and defect will be determined on an N-type silicon substrate with the lifetime controlled for IGBT. The oxygen concentration is in an order of the 17th power to the 18th power per 1 $cm^3$, for example, when produced by a CZ method; and is approximately in a higher end of the 15th power to the 16th power per 1 $cm^3$ in a FZ method, although it depends on the oxygen concentration of the raw material. The dopant concentration will be $5 \times 10^{14}$ atoms/$cm^3$ or less in phosphorous concentration, for example, assuming the resistivity range generally used as IGBT to be 10 Ωcm or more. Although the formed amount of monovacancies largely differs based on the irradiation quantity of a particle beam and is difficult to be evaluated, herein, an example is assumed in such a way that the irradiation is performed so as to form approximately $1 \times 10^{13}$ to $1 \times 10^{15}$/$cm^3$ of Frenkel pairs in a crystal.

In the foregoing condition, since the oxygen concentration is sufficiently high to the phosphorous concentration [P] or the V concentration [V], the reaction of (1) preferentially occurs. The reactions of (2) and (3) occurs in the remained V. That is, in a crystal with a high oxygen concentration, the reaction (1) is apt to occur, and contrarily, the reactions of (2) and (3) are hard to occur; in a crystal with a low oxygen concentration, the reactions of (2) and (3) are apt to occur in place of the reaction (1) being suppressed. In the VP and the VV, which are products of the reactions (2) and (3), it is considered that the concentrations [VP] and [VV] are determined depending on the remained V concentration [remained V] ([remained V]∝[VP], [remained V]∝[VV]), and therefore it is possible to represent in a simple way as [remained V]∝[VP]∝[VV].

On the other hand, the VP is reported to form a level at a position of approximately 0.45 eV below the silicon conduction bond by an analysis of DLTS (Deep Level Transient Spectroscopy), and therefore is not working as an N-type dopant. That is, the resistivity of a silicon substrate increases as the formed VP amount, and accordingly the [VP] can be evaluated by measuring a rate of change of the carrier concentration before and after an irradiation. Therefore, the [VV] can be evaluated in a simple way as [VV]∝[VP]∝ the rate of the change of a carrier concentration.

The present inventors have found the foregoing, thereby brought the present invention to be completion.

The present invention will be explained specifically with reference to the figures in the following, but the present invention is not limited thereto.

First Embodiment

Figure 1:
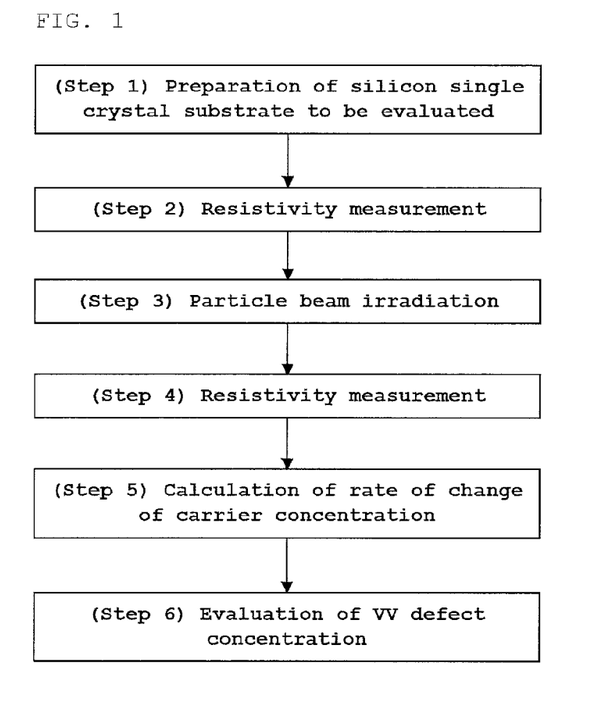
FIG. 1 is a flow chart to show an example of the steps of the method for evaluating a defect concentration in a silicon single crystal substrate of the present invention.

FIG. 1 shows an example of the steps of the method for evaluating a defect concentration in a silicon single crystal substrate of the present invention.

(Step 1: Preparation of Silicon Single Crystal Substrate to be Evaluated)

First, a silicon single crystal substrate to be evaluated (occasionally referred to as a wafer for simplicity in the following) is prepared. The silicon single crystal ingot as a raw material of the wafer can be manufactured by any one of the methods of a floating zone method (FZ method) and a Czochralski method (CZ method). The thickness or the surface treatment method of the wafer are not particularly limited.

The oxygen concentration of the wafer, though it is not particularly limited, can be set to approximately $5 \times 10^{15}$ to $2 \times 10^{18}$ atoms/$cm^3$, for example, which is a range of the wafer generally produced by a FZ method or a CZ method. In such a range, since the foregoing mechanism of the defect formation found by the present inventors tends to be more valid, though it depends on the dopant concentration and so on, the inventive evaluation method can be effectively utilized.

The conductivity type of the silicon, though it is not particularly limited, can be an N-type doped with any of phosphorous, arsenic, and antimony, for example. The dopant concentration in the crystal can be $5 \times 10^{14}$ atoms/$cm^3$ or less. This corresponds to the one with resistivity of approximately 10 Ωcm or more in case of phosphorous doping.

Regarding a reaction of a monovacancy with a dopant atom, when the atomic radius is the same or larger compared to silicon, the dopant atom forms a complex with the monovacancy to be stabilized. On the other hand, when the atomic radius is smaller than silicon, it forms a complex with an interstitial silicon to be stabilized. Accordingly, in a case of the foregoing elements such as phosphorous, arsenic, and antimony, the dopant atom can form a composite defect with the monovacancy more securely, and the foregoing mechanism tends to appear compared to a case of the element with a relatively small atomic radius such as boron.

As described above, the reason why the foregoing examples are listed as a dopant species or a range of the concentration thereof is that the mechanism of the defect formation tends to be more valid as explained on the foregoing oxygen concentration.

In the following, phosphorous doping will be explained as an example.

The wafer may be doped with nitrogen or not. The carbon concentration is not particularly limited too. That is because nitrogen and carbon are considered not to contribute to the reaction of a monovacancy V of Si. The amount of carbon, however, changes the defect amount rerate to carbon due to an interstitial silicon I. Accordingly, if this influence is considered, more precise evaluation can be obtained when the inventive defect evaluation is related to device properties.

(Step 2: Resistivity Measurement)

On the foregoing wafer, the resistivity is measured.

However, when oxygen or nitrogen is contained in the wafer, a thermal donner or an NO donner can be generated. In order to prevent the deviation of the resistivity from the intrinsic value by the donner, it is preferable to apply a donner annihilation heat treatment previously. For example, in a case of a CZ wafer without doping nitrogen, the thermal donner can be sufficiently annihilated by applying a heat treatment of 650° C. for 20 minutes, for example.

Regarding the measuring method for the resistivity, the use of a four-point probe method is simple and preferable when an electron beam is used in the subsequent particle beam irradiation, but the measuring method is not limited thereto. Particularly, in case of using an ion beam other than an electron beam, the defects in a wafer due to irradiation tend to localize to a particular depth compared to the case using an electron beam. In that case, it is preferable to use a measuring method which can examine the distribution along the depth direction such as a spreading resistance (SR) measurement after an angle polishing. As described above, the measuring method can be appropriately determined according to the irradiation condition and so on.

(Step 3: Particle Beam Irradiation)

Then, the wafer is irradiated with a particle beam.

The particle beam can be composed of an electron or an ion. These irradiation form crystal defects (Frenkel pair and VV defect due to the monovacancy thereof, etc.) in the silicon single crystal. The irradiation condition of the particle beam is not particularly limited, and the irradiation quantity can be appropriately adjusted in such a way that an appropriate amount of Frenkel pairs are formed and the foregoing mechanism is valid. Although it is difficult to calculate a vacancy concentration from the irradiation quantity, in an electron beam irradiation, it is preferable to set the irradiation quantity to be $1\times10^{16}/cm^2$ or less at an acceleration voltage of 2 MV.

(Step 4: Resistivity Measurement)

Then, the resistivity is measured again on the wafer after irradiating a particle beam.

In an actual use as a device, annealing is usually performed after the irradiation to remove useless damages. In this case, however, the heat treatment is needless since the purpose is to evaluate the damage. However, as a matter of course, it is also possible to perform the heat treatment as the need arises.

(Step 5: Calculation of Rate of Change of Carrier Concentration)

On the basis of the resistivities before and after the irradiation, the carrier concentrations before and after the irradiation are calculated respectively by using an Irvin curve and so on, and further calculate a rate of change of the carrier concentration. The rate of the change of the carrier concentration can be determined by the following equation, for example.

Rate of change of carrier concentration=$([n]_f-[n]_i)/[n]_i \times 100$

Herein, $[n]_i$ is a carrier concentration before the irradiation, and $[n]_f$ is a carrier concentration after the irradiation.

(Step 6: Evaluation of VV Defect Concentration)

By using the rate of the change of the carrier concentration calculated as described above, the VV defect concentration is evaluated.

Herein, a relation between the rate of the change of a carrier concentration and an oxygen concentration or irradiation quantity of the particle beam are explained at first.

Figure 2:
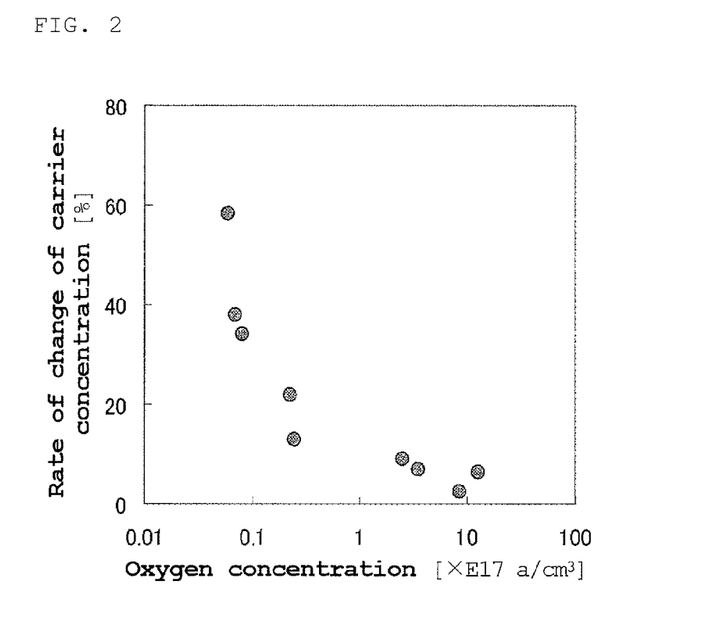
FIG. 2 is a graph to show a relation between a rate of change of a carrier concentration and an oxygen concentration.

FIG. 2 shows a correlation between an oxygen concentration and a rate of change of a carrier concentration. This is the results of performing an irradiation with an electron beam of $6\times10^{14}/cm^2$ to each of phosphorous doped N-type wafers (resistivity: approximately 60 Ωcm) with various oxygen concentrations produced by a FZ method and a CZ method.

As can be revealed by this FIG. 2, the rate of the change of the carrier concentration comes to be smaller as the oxygen concentration gets higher. This indicates that more monovacancies Vs are consumed by O as the oxygen concentration gets higher, and accordingly the monovacancy comes to be hard to form the complex PV with phosphorous as the foregoing consideration by the present inventors.

Figure 3:
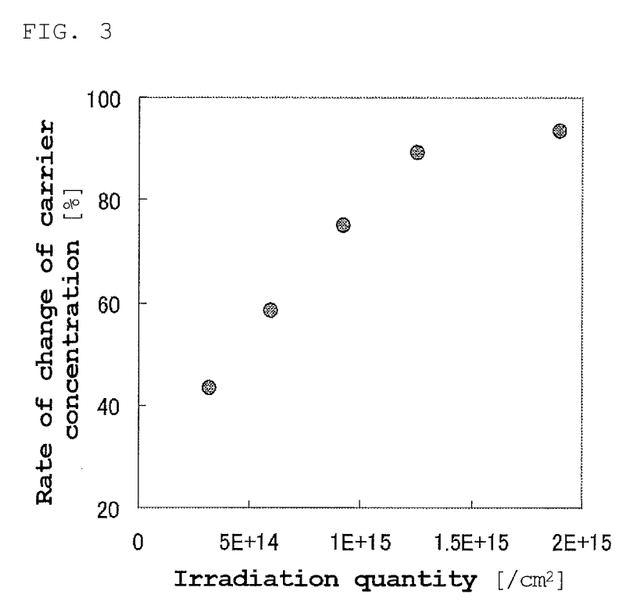
FIG. 3 is a graph to show a relation between the rate of the change of a carrier concentration and a irradiation quantity of an electron beam.

FIG. 3 shows a correlation between an irradiation quantity of an electron beam and a rate of change of a carrier concentration. All of the oxygen concentrations of the wafers are $6\times10^{15}$ atoms/$cm^3$.

From this FIG. 3, it can be said that as the irradiation quantity of an electron beam increases, the defect number increases, and the carrier concentration changes more largely.

As shown in FIG. 2 and FIG. 3, the rate of the change of the carrier concentration varies depending on the oxygen concentration and the irradiation quantity of the particle beam. Herein, it is considered that $[VP]\propto[VV]$ as described above, and accordingly it can be understood indirectly that in a wafer with a higher rate of change of the carrier concentration, more VV defects are formed. As described above, it is possible to evaluate the VV defect concentration in a simple way by using the rate of the change of the carrier concentration. Although the specific value of the VV defect concentration is not determined, a relative VV defect concentration between each samples can be evaluated.

By obtaining datum to show the relation of an oxygen concentration or an irradiation quantity of a particle beam with a rate of change of a carrier concentration relating to a VV defect concentration such as FIG. 2 and FIG. 3 in advance, it is possible to grasp the relation thereof with the VV defect concentration. This enables to evaluate how much irradiation quantity is required to make the irradiation damage equivalent when the oxygen concentration of a wafer is altered, for example.

It is considered that some kind of impurities may affect to the formation of irradiation defect when they are contained in a wafer in addition to the foregoing example of carbon. Accordingly, when evaluating a wafer containing high concentration of impurities which are not considered in the foregoing embodiment or a wafer with an impurity concentration which largely differs among the samples, it is possible to perform a more precise evaluation by including a step to consider the influence of these impurities, as the need arises. These consideration can be appropriately performed according to the evaluation precision, the cost, time and effort.

Second Embodiment

Figure 4:
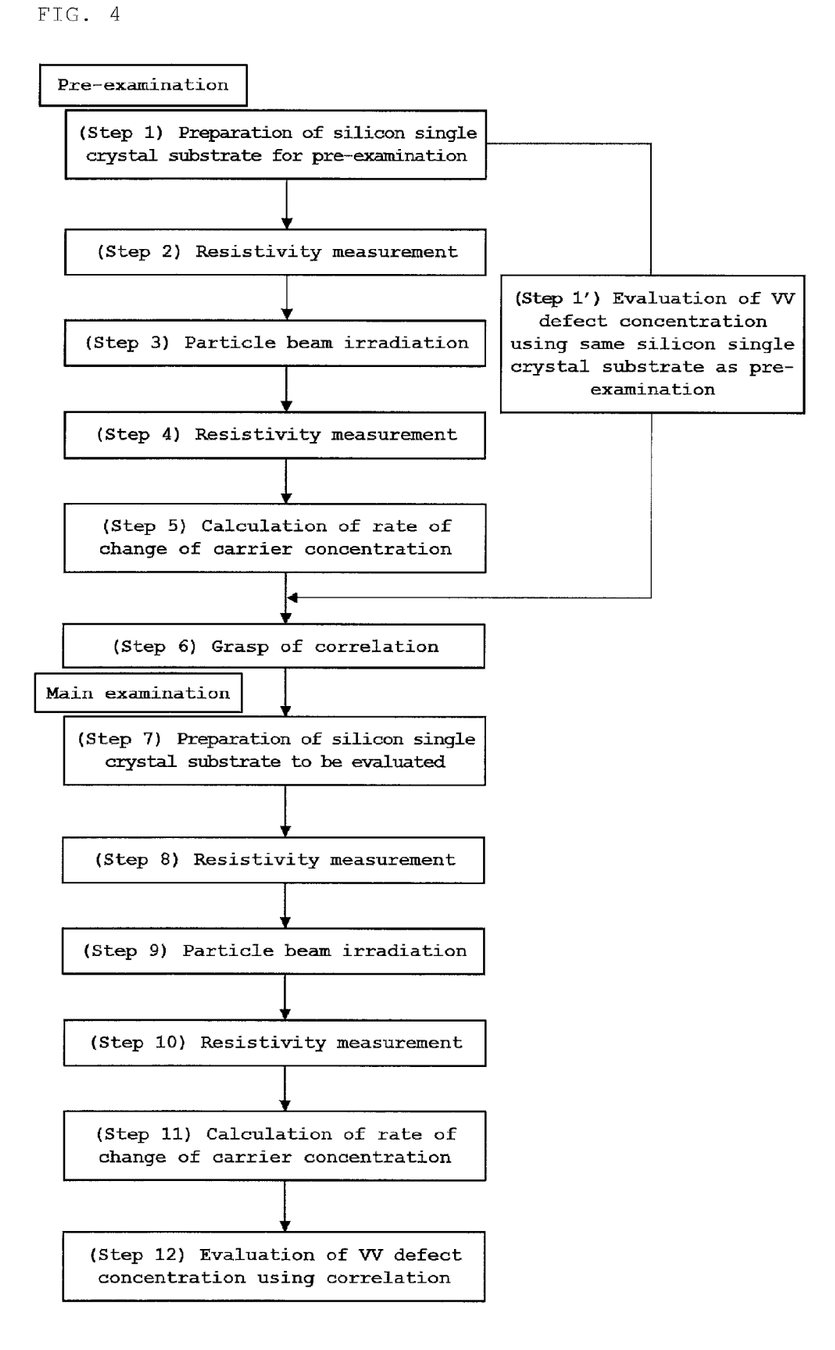
FIG. 4 is a flow chart to show another example of the steps of the method for evaluating a defect concentration in a silicon single crystal substrate of the present invention.

As another embodiment of the present invention, it is possible to perform a pre-examination before evaluating a silicon single crystal substrate to be actually evaluated. FIG. 4 shows an example of the steps of the second embodiment.
[Pre-Examination]
(Step 1: Preparation of Silicon Single Crystal Substrate for Pre-Examination)

First, a silicon single crystal substrate for the pre-examination (occasionally referred to as a pre-examination wafer for simplicity in the following) is prepared. As this pre-examination wafer, for example, the same kind of a wafer as the wafer to be evaluated being prepared later can be used except that the VV defect concentration has been already evaluated. The specifics such as an oxygen concentration can be determined as in the first embodiment, for example.

Herein, this will be explained by illustrating an example preparing plural pre-examination wafers having the same oxygen concentration, dopant species, resistivity, etc. with a wafer to be evaluated, but the number is not particularly limited.
(Step 1': Evaluation of VV Defect Concentration Using Same Silicon Single Crystal Substrate as Pre-Examination)

It is difficult to quantity the VV defect concentration directly. Then, by using the same kind of wafer as a pre-examination wafer, for example, it is possible to evaluate the VV defect concentration in the pre-examination wafer previously and indirectly on the basis of the recovery property of a diode manufactured in the manufacturing step by irradiating a particle beam in the same condition as in the particle beam irradiation step of Step 3 in a pre-examination described later. Since a VV defect in a wafer acts as a recombination center of carriers, more VV defects give shorter annihilation time and an improved recovery property. Accordingly, it is considered that the recovery property represents the amount of formed VV defects.

Herein, diodes are produced by altering the irradiation quantity for a number of pre-examination wafers, and on each of these diodes, a recovery property is determined previously as an indication of the VV defect concentration in each pre-examination wafer.

As a matter of course, it is possible to use other parameters which correspond to the VV defect concentration other than this recovery property.
(Step 2 to Step 5: Resistivity Measurement to Calculation of Rate of Change of Carrier Concentration)

On each pre-examination wafer, resistivity measurement, particle beam irradiation, and re-measurement of resistivity are performed to determine the carrier concentrations in each pre-examination wafer before and after the irradiation, and each rate of change of the carrier concentration is calculated.

In Step 3 (particle beam irradiation), the particle beam is irradiated in the same condition with the manufacturing step of diode in the foregoing Step 1'. In this case, the irradiation quantity differs for each pre-examination wafer.

The specific processes in these steps can be performed in the same way of the first embodiment, for example.

(Step 6: Grasp of Correlation)

A correlation between the VV defect concentration (herein, quality of recovery property of the diode) and the rate of the change of the carrier concentration in each pre-examination wafer calculated as described above is determined. This enables to obtain the VV defect concentration (the quality of the recovery property of the diode) corresponding to each rate of the change of the carrier concentration when the oxygen concentration and so on are the same condition.
[Main Examination]
(Step 7 to Step 11: Preparation of Silicon Single Crystal Substrate to be Evaluated to Calculation of Rate of Change of Carrier Concentration)

Then, the main examination is performed. That is, an evaluation of the wafer to be actually evaluated is performed. The wafer to be evaluated is prepared, and is subjected to resistivity measurement, particle beam irradiation with a prescribed irradiation quantity, and re-measurement of resistivity. Carrier concentrations in the wafer to be evaluated before and after the irradiation are determined to calculate the rate of change of the carrier concentration.
(Step 12: Evaluation of VV Defect Concentration Using Correlation)

The VV defect concentration of the wafer to be evaluated (herein, quality of recovery property of the diode) is evaluated by using the rate of the change of the carrier concentration calculated as described above and the correlation determined in the pre-examination. That is, the calculated rate of the change of the carrier concentration is applied to the foregoing correlation to determine the corresponding VV defect concentration (the quality of the recovery property). In this way, it is possible to perform a relative evaluation of the VV defect concentration in a simple way by using the pre-examination.

Incidentally, it is not need to perform the pre-examination every time. It is possible to use a collected previous datum to show a correlation between the rate of the change of the carrier concentration and the VV defect concentration. In this case, the steps to be required in the pre-examination can be omitted, and the evaluation can be performed more simply.

EXAMPLE

The present invention will be more specifically described below with reference to Examples and Comparative Example, but the present invention is not limited thereto.

Example 1

By using CZ method and FZ method, respectively, a phosphorous doped silicon single crystal ingots with a diameter of 200 mm were manufactured. The oxygen concentrations in the crystals measured by an FT-IR method were $3.5 \times 10^{17}$ atoms/cm$^3$ in the CZ crystal and $0.3 \times 10^{17}$ atoms/cm$^3$ in the FZ crystal. Each of the resistivity was approximately 60 Ωcm. Incidentally, the carbon concentrations were decreased to approximately $5 \times 10^{14}$ atoms/cm$^3$ in order to avoid the occurrence of defects relate to carbon, which affect to the device properties.

First, polished wafers (PW) were produced from the FZ crystal. Subsequently, PN diodes were produced from those FZ wafers. To those diodes, electron beam irradiations at 5 levels were performed with an acceleration voltage of 2 MV in the producing step, respectively.

The amount of formed VV defect was evaluated indirectly on the basis of a recovery property of the produced diode, since it is difficult to quantity the amount of formed VV defect directly as described above. It is considered that quality of the recovery property represents the magnitude of the VV defect concentration. The evaluation results are shown in Table 1.

On the other hand, to the same kind of PW as the foregoing PW, the electron beam irradiations at 5 levels were performed in the same condition with the production of the diodes, and the resistivities before and after the irradiation were measured by a four-point probe method. On the basis of the measurement, the carrier concentrations before and after the irradiation were determined. The rate of the change of the carrier concentration calculated therefrom is also shown in Table 1.

TABLE 1

| Manufacture method of crystal | Irradiation level | Irradiation quantity [/cm$^2$] | Recovery property | Rate of change of carrier concentration (%) |
|---|---|---|---|---|
| FZ | 1 | 2E+14 | Fail | 17.7 |
| FZ | 2 | 5E+14 | Fail | 23 |
| FZ | 3 | 1E+15 | Success | 28.8 |
| FZ | 4 | 2E+15 | Success | 33.2 |
| FZ | 5 | 4E+15 | Success | 41.3 |

Table 1 has revealed the correlation between the VV defect concentration (quality of recovery property) and the rate of the change of the carrier concentration determined as described above. It was also revealed that the recovery property resulted in success when the rate of the change of the carrier concentration was approximately 29% or more.

The evaluation of the VV defect concentration (recovery property evaluation) and the calculation of the rate of the change of the carrier concentration were performed on the CZ wafers, which are polished wafers (PW) produced from the CZ crystal, in the same manner as in the foregoing. The results are shown in Table 2.

TABLE 2

| Manufacture method of crystal | Irradiation level | Irradiation quantity [/cm$^2$] | Recovery property | Rate of change of carrier concentration (%) |
|---|---|---|---|---|
| CZ | 1 | 2E+14 | Fail | 8.6 |
| CZ | 2 | 5E+14 | Fail | 11.2 |
| CZ | 3 | 1E+15 | Fail | 17.6 |
| CZ | 4 | 2E+15 | Fail | 22.9 |
| CZ | 5 | 4E+15 | Success | 29.3 |

As can be seen from Table 2, it was when the rate of the change of the carrier concentration was approximately 29% or more that the recovery property resulted in success as in the case of FZ wafers.

From these Table 1 and Table 2, it can be said that the damage amount evaluated on the basis of the rate of the change of the carrier concentration is an effective indication. That is, it has been found that evaluating the VV defect concentration on the basis of the rate of the change of the carrier concentration as in the present invention is an effective method. Furthermore, it is possible to grasp the relation between the irradiation quantity and the VV defect concentration in the oxygen concentration and so on in each prepared CZ wafers and FZ wafers as in Table 1 and Table 2.

Example 2

On each of the FZ wafer and the CZ wafer which were prepared separately from the foregoing (their oxygen concentration and so on were the same with the ones prepared to make Table 1 and Table 2), an electron beam was irradiated in an irradiation quantity different from the irradiation levels described in Table 1 and Table 2. Their rate of change of the carrier concentration were calculated, considering these Table 1 and Table 2 as the results of the pre-examination. The both of these rates were 29% or more. Accordingly, by considering these calculation results of the carrier concentrations and Table 1 and Table 2 of the pre-examination, each recovery property was evaluated to be success when producing a PN diode by irradiating the same kind of wafer as these wafers with an electron beam having the same irradiation quantity.

When the PN diodes were actually produced, the evaluated recovery properties were success as had been pre-evaluated.

Comparative Example

The same kind of FZ wafers and CZ wafers as in Example 1 were prepared.

First, the PN diodes were produced by simply irradiating the FZ wafers with electron beam having an irradiation quantity as described in Table 1 (irradiation levels of 1 to 5) without performing resistivity measurements and calculations of rate of change of a carrier concentration unlike Example 1, and the relation between the irradiation quantities and quality of the recovery properties was obtained. This relation was similar to the one shown in Table 1.

Accordingly, in case of producing PN diodes from the CZ wafers as in the same manner to the FZ wafers, each quality of the recovery property of the PN diodes based on the CZ wafers was evaluated to be the same as in the FZ wafers with the same irradiation quantity.

Actually, however, the relation between the irradiation quantity and the quality of the recovery property fell on the results shown in Table 2. That is, as proved by the results of irradiation level 3 and 4, for example, despite that the recovery properties were success in the FZ wafers, the results in the CZ wafers were failure contrary to the expectations. As the foregoing, the device property can be different from each other in the wafers having different oxygen concentrations due to the difference of each irradiation damage even when the irradiation conditions are same.

As can be seen from the evaluation results of such Comparative Example, which only considers irradiation condition, compared with that of Examples 1 and 2 performing the present invention, the present invention, which considers the rate of the change of the carrier concentration when evaluating the VV defect concentration, is effective as described above.

It is to be noted that the present invention is not limited to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:
1. A method for evaluating a concentration of a defect in a silicon single crystal substrate, the defect being formed by particle beam irradiation in the silicon single crystal substrate, comprising the steps of:

measuring a resistivity of the silicon single crystal substrate, followed by irradiating the silicon single crystal substrate with the particle beam, re-measuring resistivity of the silicon single crystal substrate after the irradiation;

determining each carrier concentration in the silicon single crystal substrate before and after the irradiation on the basis of the measured results of resistivity before and after the particle beam irradiation to calculate a rate of change of the carrier concentration; and evaluating a concentration of a VV defect on the basis of the rate of the change of the carrier concentration, the VV defect being comprised of a silicon atom vacancy and being formed by the particle beam irradiation in the silicon single crystal substrate.

2. The method for evaluating a concentration of a defect in a silicon single crystal substrate according to claim 1, wherein the particle beam to irradiate the silicon single crystal substrate is composed of an electron or an ion.

3. The method for evaluating a concentration of a defect in a silicon single crystal substrate according to claim 2, wherein a dopant impurity contained in the silicon single crystal substrate is any of phosphorous, arsenic, and antimony.

4. The method for evaluating a concentration of a defect in a silicon single crystal substrate according to claim 3, further comprising the steps of:

preparing a silicon single crystal substrate for pre-examination with a pre-evaluated concentration of the VV defect separately from the silicon single crystal substrate to be evaluated;

determining a correlation on the basis of the pre-evaluated concentration of the VV defect and a rate of change of a carrier concentration before and after the particle beam irradiation with respect to the silicon single crystal substrate for pre-examination; and irradiating the silicon single crystal substrate to be evaluated with the particle beam to evaluate the concentration of the VV defect by using the correlation.

5. The method for evaluating a concentration of a defect in a silicon single crystal substrate according to claim 2, further comprising the steps of:

preparing a silicon single crystal substrate for pre-examination with a pre-evaluated concentration of the VV defect separately from the silicon single crystal substrate to be evaluated;

determining a correlation on the basis of the pre-evaluated concentration of the VV defect and a rate of change of a carrier concentration before and after the particle beam irradiation with respect to the silicon single crystal substrate for pre-examination; and irradiating the silicon single crystal substrate to be evaluated with the particle beam to evaluate the concentration of the VV defect by using the correlation.

6. The method for evaluating a concentration of a defect in a silicon single crystal substrate according to claim 1, wherein a dopant impurity contained in the silicon single crystal substrate is any of phosphorous, arsenic, and antimony.

7. The method for evaluating a concentration of a defect in a silicon single crystal substrate according to claim 6, further comprising the steps of:

preparing a silicon single crystal substrate for pre-examination with a pre-evaluated concentration of the VV defect separately from the silicon single crystal substrate to be evaluated;

determining a correlation on the basis of the pre-evaluated concentration of the VV defect and a rate of change of a carrier concentration before and after the particle beam irradiation with respect to the silicon single crystal substrate for pre-examination; and irradiating the silicon single crystal substrate to be evaluated with the particle beam to evaluate the concentration of the VV defect by using the correlation.

8. The method for evaluating a concentration of a defect in a silicon single crystal substrate according to claim 1, further comprising the steps of:

preparing a silicon single crystal substrate for pre-examination with a pre-evaluated concentration of the VV defect separately from the silicon single crystal substrate to be evaluated;

determining a correlation on the basis of the pre-evaluated concentration of the VV defect and a rate of change of a carrier concentration before and after the particle beam irradiation with respect to the silicon single crystal substrate for pre-examination; and irradiating the silicon single crystal substrate to be evaluated with the particle beam to evaluate the concentration of the VV defect by using the correlation.

* * * * *